United States Patent [19]

Noguchi et al.

[11] 4,105,670
[45] Aug. 8, 1978

[54] SPIRO[CYCLOPROPANE-1,2'-INDOLIN]-3'-ONES

[75] Inventors: Shunsaku Noguchi, Minoo; Saburo Takei, Tokyo; Yasuhiko Kawano, Nishinomiya, all of Japan

[73] Assignee: Takeda Chemical Industries, Ltd., Japan

[21] Appl. No.: 743,404

[22] Filed: Nov. 19, 1976

[30] Foreign Application Priority Data

Nov. 26, 1975 [JP] Japan .............................. 50-141748

[51] Int. Cl.² ........................................... C07D 209/04
[52] U.S. Cl. ....................... 260/326.11 R; 260/239 B; 260/293.61; 260/313.1; 260/343.3 R; 424/274
[58] Field of Search .............................. 260/326.11 R

[56] References Cited
PUBLICATIONS
Chem. Abstracts 66:289532.

Primary Examiner—Ethel G. Love
Attorney, Agent, or Firm—Wenderoth, Lind & Ponack

[57] ABSTRACT

Spiro[cyclopropane-1,2'-indolin]-3'-ones of the general formula:

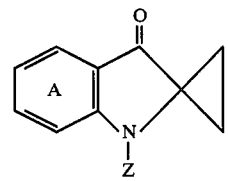

wherein the ring A is a substituted or unsubstituted phenyl ring and Z is hydrogen, a substituted or unsubstituted alkyl group or a substituted or unsubstituted acyl group and their pharmaceutically acceptable salts have gastric acid secretion suppressing activity, antiinflammatory activity and analgesic activity.

32 Claims, No Drawings

SPIRO[CYCLOPROPANE-1,2'-INDOLIN]-3'-ONES

The present invention relates to spiro-compounds. More particularly, the invention relates to a spiro(cyclopropane-1,2'-indolin)-3'-ones of the general formula (I)

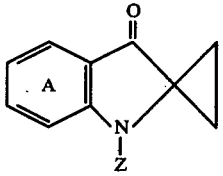

wherein the ring A may optionally be substituted; Z is hydrogen, an alkyl group which may optionally be substituted or an acyl group which may optionally be substituted and their pharmaceutically acceptable salts.

Those compounds are novel compounds which have not been described in the literature and, by virtue of their excellent gastric acid secretion suppressing action, antiinflammatory action and analgesic action, are of use as drugs for man and other warm-blooded animals (typically mice, rats, guinea-pigs, etc.).

The ring A may be an unsubstituted or substituted phenyl. When it is substituted, the substituent is exemplified by alkyl group having 1 to 4 carbon atoms (e.g. methyl, ethyl, n-propyl, isopropyl, n-butyl, isobutyl, t-butyl, sec-butyl, etc.), an alkoxy group having 1 to 4 carbon atoms (e.g. methoxy, ethoxy, n-propoxy, isopropoxy, n-butoxy, isobutoxy, t-butoxy, sec-butoxy, etc.), an alkylenedioxy group having 1 to 4 carbon atoms (e.g. methylenedioxy, etc.), hydroxyl, nitro, amino, formyl amino, an alkylcarbonyl amino group having 2 to 5 carbon atoms (e.g. acetylamino, propionylamino, n-butyrylamino, etc.), an arylcarbonyl amino group having 7 to 11 carbon atoms (e.g. benzoylamino, naphthoylamino, etc.), halogen (e.g. fluorine, chlorine, bromine, etc.) and so forth. The number of substituent on the ring A may range from 0 to 4 and, where 2 to 4 substituents occur, they may be the same substituent or different substituents.

The alkyl group designated by Z has 1 to 4 carbon atoms and is exemplified by methyl, ethyl, n-propyl, isopropyl, n-butyl, sec-butyl, t-butyl, isobutyl, etc. Any of these alkyls may have appropriate one or more of substituents. The substituent is exemplified by (1) an aryl group having 6 to 10 carbon atoms (e.g. phenyl, naphthyl, etc.), which may be substituted by halogen (e.g. chlorine, bromine, fluorine, etc.), an alkyl group having 1 to 4 carbon atoms (e.g. methyl, ethyl, n-propyl, etc.) or an alkoxy group having 1 to 4 carbon atoms (e.g. methoxy, ethoxy, n-propoxy, etc.);
(2) an alkylcarbonyl group having 2 to 5 carbon atoms (e.g. acetyl, n-propionyl, isopropionyl, n-butyryl, etc.) or formyl, etc.;
(3) an arylcarbonyl group having 7 to 11 carbon atoms (e.g. benzoyl, naphthoyl, etc.), which may be substituted by a halogen (e.g. chlorine, bromine, etc.), the typical substituent being p-halogenobenzoyl;
(4) an alkoxy group having 1 to 4 carbon atoms (e.g. methoxy, ethoxy, n-propoxy, isopropoxy, etc.);
(5) hydroxyl;
(6) an alkoxycarbonyl group having 2 to 5 carbon atoms (e.g. methoxycarbonyl, ethoxycarbonyl, etc.);
(7) carboxyl;
(8) an N-substituted or unsubstituted carbamoyl group of the formula;

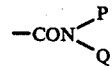

wherein each of P and Q is hydrogen or an alkyl group having 1 to 4 carbon atoms (e.g. methyl, ethyl, n-propyl, isopropyl, etc.) or alternatively P and Q, taken together, form an alkylene group having 4 to 6 carbon atoms (e.g. —(CH$_2$)$_4$—, —(CH$_2$)$_5$—, —(CH$_2$)$_6$—, etc.);
(9) amino;
(10) a mono- or di-alkylamino group in which the alkyl has 1 to 4 carbon atoms (e.g. monomethylamino, dimethylamino, diethylamino, etc.); etc.

The preferable number of the substituent of the alkyl Z is one. The acyl group Z is exemplified by
(1) a carboxylic acid residue of the formula: R$^1$CO- in which R$^1$ is hydrogen, an alkyl group having 1 to 4 carbon atoms (e.g. methyl, ethyl, n-propyl, isopropyl, n-butyl, t-butyl, sec-butyl, isobutyl, etc.), an alkoxy group having 1 to 4 carbon atoms (e.g. methoxy, ethoxy, n-propoxy, etc.) or an aryl group having 6 to 10 carbon atoms (e.g. phenyl or naphthyl);
(2) a sulfonic acid residue of the formula: R$^2$SO$_2$- in which R$^2$ is an alkyl group having 1 to 4 carbon atoms (e.g. methyl, ethyl, etc.) or an aryl group having 6 to 10 carbon atoms (e.g. phenyl, naphthyl, etc.); or
(3) a carbamic acid residue of the formula:

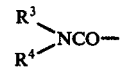

in which each of R$^3$ and R$^4$ is hydrogen, an alkyl group having 1 to 4 carbon atoms (e.g. methyl, ethyl, n-propyl, etc.) or an aryl group having 6 to 10 carbon atoms (e.g. phenyl, naphthyl, etc.).

The each of the substituents of the acyl Z, i.e. R$^1$, R$^2$, R$^3$, and R$^4$, except in case when R$^1$, R$^2$, R$^3$ or R$^4$ is hydrogen, may have further one substituent, which is exemplified by
(1) amino;
(2) a mono- or di-alkylamino, the alkyl having 1 to 4 carbon atoms, (e.g. monomethylamino, dimethylamino, etc.) or a substituted amino of the formula:
—N̈(CH$_2$)$_m$
in which m is an integer from 4 to 6 (e.g.
—N̈(CH$_2$)$_4$, —N̈(CH$_2$)$_5$, —N̈(CH$_2$)$_6$,
etc.);
(3) an alkyl group having 1 to 4 carbon atoms (e.g. methyl, ethyl, n-propyl, etc.);
(4) an alkoxy group having 1 to 4 carbon atoms (e.g. methoxy, ethoxy, n-propoxy, etc.);
(5) halogen (e.g. fluorine, chlorine, bromine, etc.); or
(6) a substituted carbamoyl of the formula:

In which P and Q, taken together, form an alkylene group having 4 to 6 carbon atoms (e.g. —(CH$_2$)$_4$—, —(CH$_2$)$_5$—, —(CH$_2$)$_6$—, etc.).

The preferred class among the compounds (I) is shown by the general formula:

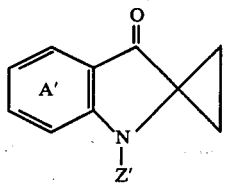

The ring A' is a phenyl ring which may be substituted by one or two substituents. The substituent is exemplified by an alkyl group having 1 to 4 carbon atoms, an alkoxy group having 1 to 4 carbon atoms or halogen. The substituent Z' may be hydrogen or an alkyl group having 1 to 4 carbon atoms, which may be further substituted by (1) a di-alkylamino group in which the each alkyl of the di-alkylamino group has 1 to 4 carbon atoms;
(2) an alkoxycarbonyl group having 2 to 5 carbon atoms;
(3) benzoyl which may be substituted by a halogen;
(4) phenyl which may be substituted by an alkoxy group having 1 to 4 carbon atoms;
(5) hydroxyl;
(6) carboxyl; or
(7) an N-substituted carbamoyl group of the formula:

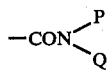

in which P and Q, taken together, form an alkylene group having 4 to 6 carbon atoms.

The substituent Z' may be (1) an acyl group of the formula: R$^1$CO— in which R$^1$ is hydrogen; an alkoxy group having 1 to 4 carbon atoms; a phenyl group which may be substituted by a halogen; or an alkyl group having 1 to 4 carbon atoms which may be substituted by a dialkyl amino group, the alkyl of the dialkylamino having 1 to 4 carbon atoms or a substituted amino group of the formula: —N(CH$_2$)$_m$ in which m is an integer from 4 to 6;
(2) an acyl group of the formula: R$^2$SO$_2$— in which R$^2$ is an alkyl group having 1 to 4 carbon atoms, phenyl or a phenyl group substituted by an alkyl group having 1 to 4 carbon atoms; or
(3) an acyl group of the formula:

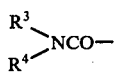

in which each of R$^3$ and R$^4$ is hydrogen or an alkyl group having 1 to 4 carbon atoms.

Examples of (1) the substituents Z', (2) the substituents of the substituents Z' and (3) the substituents of the ring A' are the same as those mentioned in the corresponding parts regarding the above Z and ring A.

The phamaceutically acceptable salts of the objective compounds of the invention include inorganic acid addition salts such as hydrochloric acid salt, sulfuric acid salt, hydrobromic acid salt, nitric acid salt, etc. and organic acid addition salts such as maleic acid salt, fumaric acid salt, oxalic acid salt, p-toluenesulfonic acid salt, methanesulfonic acid salt, malic acid salt, etc.

The objective compound of the present invention may be produced by subjecting a 4,5-dihydrospiro(furan-3(3H), 2'-indoline)-2,3'-dione of general formula (II) to a decarboxylation reaction.

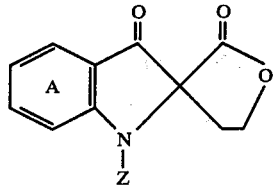

(wherein the ring A and Z are as defined in formula [I]).

The above-mentioned decarboxylation reaction is normally conducted in the presence of a catalyst which promotes decarboxylation. Among preferred catalysts of the described type are metal halides (e.g. sodium chloride, sodium bromide, sodium iodide, potassium bromide, potassium chloride, potassium iodide, etc.), quaternary ammonium salts (e.g tetramethylammonium bromide, etc.) and so forth. The amount of the catalyst relative to the starting compound [II] is 0.1 to 10 equivalent mols.

The reaction temperature may be normally in the range of about 100° to 200° C and, preferably, in the range of 140° to 160° C, although a higher or lower temperature may of course be employed. It should be understood, however, that the reaction will be too slow at low temperatures while a decomposition reaction may arise at excessively elevated temperatures. There also are cases in which the replacement of the air in the reaction vessel with an inert gas such as nitrogen or argon gas results in a successful suppression of side reactions and, hence, in an improved yield.

Normally the reaction is preferably carried out in a conventional solvent. Particularly desirable, however, is a solvent boiling at a temperature about 140° C or up (e.g. N,N-dimethylformamide, dimethyl sulfoxide, hexamethylphosphoramide, etc.).

It has never been known that a cyclic ester compound of the formula:

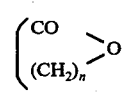

may be decarboxylated to produce a cyclic hydrocarbon compound of the formula:

[I']

Our research into derivatives of compound [II'] led to the finding that derivatives within a limited range could be decarboxylated to cyclic hydrocarbons. Thus, it was discovered that a spiro compound of the aforementioned formula [I] could be successfully produced by decarboxylating a compound of formula [II] which is a compound obtainable by introducing a specific acyl group into the 3-position of a compound of general formula [II'] where n=3. This invention is, therefore, also concerned with a method of producing new spiro compounds through a novel reaction.

It should be understood that the production of the objective compound according to this invention may also be accomplished by introducing, in a manner which is conventional per se, a substituent group designated by Z" as defined below into the imino group of a spiro[cyclopropane-1,2'-indolin]-3'-one of general formula [III]:

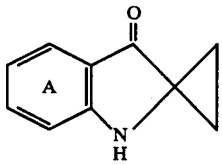

[wherein the ring A is as previously defined regarding the general formula [I]]. In this manner is produced a spiro[cyclopropane-1,2'-indolin]-3'-one of general formula [IV]:

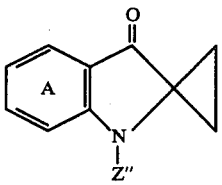

[wherein Z" is an alkyl group which may optionally be substituted or an acyl group which may optionally be substituted]. The definition of Z" in general formula [IV] is exactly the same as the definition of Z in general formulas [I] and [II] provided that a hydrogen atom has been omitted. Therefore, the alkyl group which may optionally be substituted and the acyl group which may optionally be substituted are the same as those mentioned as Z.

The means of introducing said group Z" into the imino group are well known to those skilled in the art and the method of the present invention may be carried into practice by way of such means known per se.

Thus, because the substituent group to be introduced is an alkyl group which may optionally be substituted or an acyl group which may optionally be substituted, use may be made of an alkylation or acylation procedure for the purpose.

As a representative of the alkylation procedure may be mentioned a reaction of a compound designated by Z"—X (where Z" is as defined hereinbefore, X is a halogen atom which is preferably iodine, chlorine or bromine) or a corresponding alkyl sulfate of the formula Z"$_2$SO$_4$ (wherein Z" has the same meaning as defined above) with a compound of general formula [III]. The reaction temperature in this case is normally within the range of about 0° to 100° C, while use may be made of any conventional reaction solvent. Thus, dimethyl sulfoxide, N,N-dimethylformamide, etc. may be mentioned as preferred examples and, in such cases as above, the reaction normally goes to conclusion within the time range of about 5 minutes to 1 hour. The reaction is preferably conducted in the presence of an acid acceptor, preferably a strong base, such as a sodium alkoxide, sodium hydride or alkyl-lithium (e.g. methyllithium).

The introduction of an acyl group designated by Z" may also be carried out in a manner conventional per se. As representative of such known procedure, there may be mentioned a reaction of an acid Z"OH, corresponding to the acyl group, or a reactive derivative of said acid [e.g. acid halide, acid anhydride, active ester (pentachlorophenol ester, nitrophenol ester, etc.), azide, etc.] with a compound of general formula [III]. The above procedure is particularly effective where Z" is an organic carboxylic acid residue or an organic sulfonic acid residue. Where the acid Z"OH as such is employed, the reaction is normally conducted in the presence of a dehydrating agent such as N,N'-dicyclohexylcarbodiimide. Normally the reaction temperature is within the range of about 0° to 50° C and a conventional solvent such as benzene, toluene, ethyl ether, pyridine, chloroform or methylene chloride is employed. Where an acid halide is employed on the other hand, the reaction is preferably carried out in the presence of an inorganic base such as sodium bicarbonate or an organic base such as triethylamine or pyridine. In many instances the reaction goes to conclusion within one hour.

Where Z" is a carbamic acid residue designated by $R^3R^4NCO$—, the desired compound may for example be obtained by reacting a compound of general formula [III] with a compound of the formula X—CO—X (where X is halogen) and, then, reacting the resultant compound of general formula [V]:

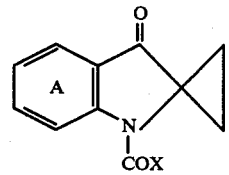

[wherein the ring A and X are as defined hereinbefore] with an amine represented by the formula $R^3R^4NH$ (wherein $R^3$ and $R^4$ are as defined hereinbefore). The first reaction step is normally carried out at a temperature within the range of about 0° to 50° C and in a conventional solvent such as benzene, toluene, ethyl ether or carbon tetrachloride, while the second step is performed normally at a temperature within the range of about 0° to 50° C and preferably in the same solvent as that used in the first reaction step. Both of these reaction steps are preferably carried out in the presence of an acid acceptor such as an inorganic base (e.g. sodium bicarbonate) or an organic base (e.g. triethylamine or pyridine).

The desired compound may also be obtained by reacting a compound of general formula [III] with a compound of the formula $R^3R^4NCOX$ (wherein $R^3$, $R^4$ are as defined hereinbefore; X is halogen).

Normally, this reaction is preferably conducted in the presence of an inorganic base such as sodium bicarbonate or an organic base such as triethylamine, pyridine or the like and in a suitable solvent such as benzene or toluene, at a temperature within the range of 0° to 100° C.

Further, where Z" is a carbamic acid residue designated by the formula $R^3R^4NCO$—and either one of $R^3$ and $R^4$ is a hydrogen atom with the other being not hydrogen but an alkyl group or an aryl group, for instance, the acylation may be advantageously accomplished by reacting the compound of general formula [III] with an isocyanate of the formula $R^5NCO$ (wherein $R^5$ is an alkyl group or an aryl group, for instance). This reaction is normally carried out at a temperature within the range of about 0° to 100° C and goes to conclusion in a short period of time within 24 hours.

Where the alkyl or acyl group is substituted by an amino group, a preferred procedure, of course, consists of protecting the amino group with a suitable protective group such as benzyloxycarbonyl prior to the introduction of a substituent, introducing the substituent into the imino group and, thereafter, removing the protective group, for example through catalytic reduction according to the conventional manners.

Where the alkyl or acyl group is substituted by a hydroxyl or carbonyl group, one may follow the procedure, prior to the introduction of a substituent, of protecting the hydroxyl, with acetyl, tetrahydropyranyl or the like, or the carbonyl group with ethyleneacetal or the like, following introduction of the substituent Z", and finally removing the protective group by way of hydrolysis or other conventional means.

The product compound of the present invention is normally formed in the reaction mixture in the form of a free base. If desired the free base may be converted into the above-mentioned pharmaceutically acceptable salt according to a per se known method.

The product compound produced in the manner described hereinbefore may be separated and purified by conventional separatory procedures such as distillation, recrystallization and column chromatography.

The compounds according to the present invention have gastric acid secretion suppressive, antiinflammatory and analgesic activities and are of value as drugs for warm-blooded animals such as man, rats, mice and guinea-pigs. Where one of the compounds is employed as an antiinflammatory agent or an analgesic, it may be orally administered to the above hosts in a daily dose of about 1 to 30 mg/kg. The compounds of the present invention are considerably low toxic, and they can be administered quite safely in the above manner. Normally, in the above application, the compound is first formed into tablets or powders in combination with a suitable excipient known per se, such as starch, prior to administration. The compound may also be administered by other routes, for example by injection or as suppositories.

Some of the starting compounds [II] used in the method according to the present invention are novel. Those novel compounds are easily produced according to the per se known methods. The processes for preparing compounds [II] are shown schematically as follows.

(1)

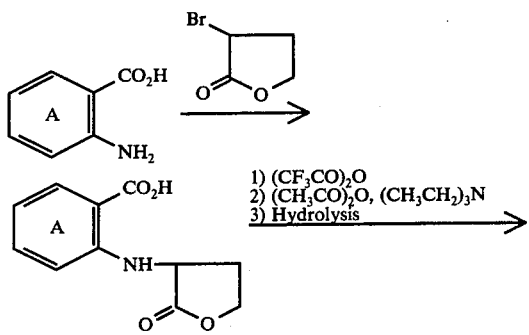

(2)

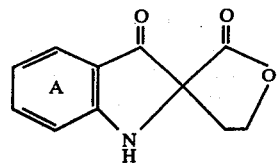

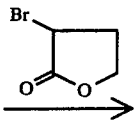

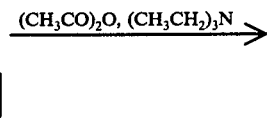

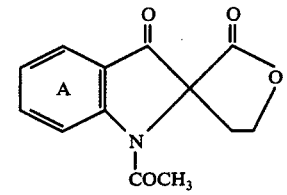

(3)

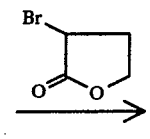

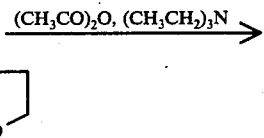

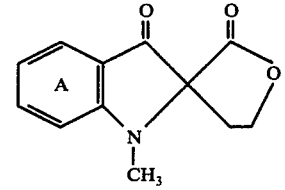

(4)

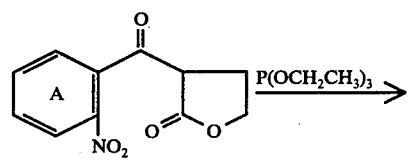

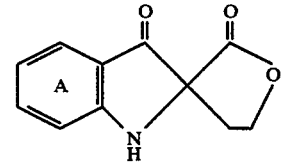

(5) By the alkylation or acylation procedure described hereinbefore, the group Z" is introduced into a compound of the general formula

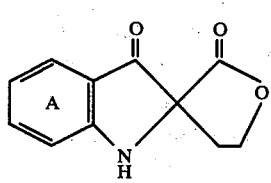

to obtain a compound of the general formula

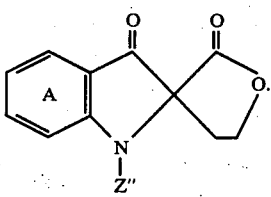

(6) One or more substituents are introduced into the benzene ring of a compound of the general formula

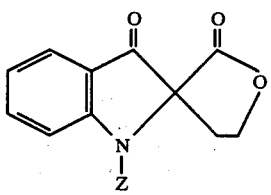

to obtain a compound of the general formula

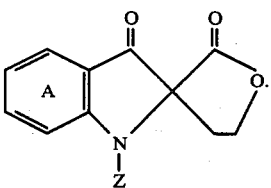

As representative compounds according to the present invention may be mentioned:—

1'-Ethyl-1'H-spiro[cyclopropane-1,2'-indolin]-3'-one;
1'-n-Propyl-1'H-spiro[cyclopropane-1,2'-indolin]-3'-one;
1'-Isopropyl-1'H-spiro[cyclopropane-1,2'-indolin]-3'-one;
1'-Phenethyl-1'H-spiro[cyclopropane-1,2'-indolin]-3'-one;
1'-Benzoyl-1'H-spiro[cyclopropane-1,2'-indolin]-3'-one;
1'-(N,N-Dimethylcarbamoyl)-1'H-spiro[cyclopropane-1,2'-indolin]-3'-one; 1'-Mesyl-1'H-spiro[cyclopropane-1,2'-indolin]-3'-one;
1'-Tosyl-1'H-spiro[cyclopropane-1,2'-indolin]-3'-one;
1'-(2-Dimethylaminopropionyl)-1'H-spiro[cyclopropane-1,2'-indolin]-3'-one; 1'-(2-Bromopropionyl)-1'H-spiro[cyclopropane-1,2'-indolin]-3'-one;
5'-Methyl-1'H-spiro[cyclopropane-1,2'-indolin]-3'-one;
1'-Acetyl-5'-methyl-1'H-spiro[cyclopropane-1,2'-indolin]-3'-one;
1'-Benzoyl-5'-methyl-1'H-spiro[cyclopropane-1,2'-indolin]-3'-one;
1'-Carbamoyl-5'-methyl-1'H-spiro[cyclopropane-1,2'-indolin]-3'-one;
5'-Methyl-1-(N-methylcarbamoyl)-1'H-spiro[cyclopropane-1,2'-indolin]-3'-one;
1'-(N,N-Dimethylcarbamoyl)-5'-methyl-1'H-spiro[cyclopropane-1,2'-indolin]-3'-one;
1'-(2-Bromopropionyl)-5'-methyl-1'H-spiro[cyclopropane-1,2'-indolin]-3'-one;
1'-(2-Dimethylaminopropionyl)-5'-methyl-1'H-spiro[cyclopropane-1,2'-indolin]-3'-one;
1'-Mesyl-5'-methyl-1'H-spiro[cyclopropane-1,2'-indolin]-3'-one;
5'-Methyl-1'-tosyl-1'H-spiro[cyclopropane-1,2'-indolin]-3'-one;
1', 5'-Dimethyl-1'H-spiro[cyclopropane-1,2'-indolin]-3'-one;
1'-Ethyl-5'-methyl-1'H-spiro[cyclopropane-1,2'-indolin]-3'-one;
5'-Methyl-1'-n-propyl-1'H-spiro[cyclopropane-1,2'-indolin]-3'-one;
5'-Methyl-1'-isopropyl-1'H-spiro[cyclopropane-1,2'-indolin]-3'-one;
1'-Ethoxycarbonylmethyl-5'-methyl-1'H-spiro[cyclopropane-1,2'indolin]-3'one;
5'-Methyl-1'-phenethyl-1'H-spiro[cyclopropane-1,2'-indolin]-3'-one;
1'-Benzyl-5'-methyl-1'H-spiro[cyclopropane-1,2'-indolin]-3'-one;
5'-Chloro-1'H-spiro[cyclopropane-1,2'-indolin]-3'-one;
1'-Acetyl-5'-chloro-1'H-spiro[cyclopropane-1,2'-indolin]-3'-one;
1'-Benzoyl-5'-chloro-1'H-spiro[cyclopropane-1,2'-indolin]-3'-one;
1'-Carbamoyl-5'-chloro-1'H-spiro[cyclopropane-1,2'-indolin]-3'-one;
5'-Chloro-1'-(N-methylcarbamoyl)-1'H-spiro[cyclopropane-1,2'-indolin]-3'-one;
5'-Chloro-1'-(N,N-dimethylcarbamoyl)-1'H-spiro[cyclopropane-1,2'-indolin]-3'-one;
1'-(2-Bromopropionyl)-5'-chloro-1'H-spiro[cyclopropane-1,2'-indolin]-3'-one;
5'-Chloro-1'-(2-dimethylaminopropionyl)-1'H-spiro[cyclopropane-1,2'-indolin]-3'-one;
5'-Chloro-1'-mesyl-1'H-spiro[cyclopropane-1,2'-indolin]-3'-one;
5'-Chloro-1'-tosyl-1'H-spiro[cyclopropane-1,2'-indolin]-3'-one;
5'-Chloro-1'-methyl-1'H-spiro[cyclopropane-1,2'-indolin]-3'-one;
5'-Chloro-1'-ethyl-1'H-spiro[cyclopropane-1,2'-indolin]-3'-one; 5'-Chloro-1'-n-propyl-1'H-spiro[cyclopropane-1,2'-indolin]-3'-one; 5'-Chloro-1'-isopropyl-1'H-spiro[cyclopropane-1,2'-indolin]-3'-one; 5'-Chloro-1'-ethoxycarbonylmethyl-1'H-spiro[cyclopropane-1,2'-indolin]3'-one; 5'-Chloro-1'-phenethyl-1'H-spiro[cyclopropane-1,2'-indolin]-3'-one; 1'-Benzyl-5'-chloro-1'H-spiro[cyclopropane-1,2'-indolin]-3'-one; 5'-Methoxy-1'H-spiro[cyclopropane-1,2'-indolin]-3'-one;
1'-Acetyl-5'-methoxy-1'H-spiro[cyclopropane-1,2'-indolin]-3'-one;
1'-Benzoyl-5'-methoxy-1'H-spiro[cyclopropane-1,2'-indolin]-3'-one; 1'-Carbamoyl-5'-methoxy-1'H-spiro[cyclopropane-1,2'-indolin]-3'-one;
5'-Methoxy-1'-(N-methylcarbamoyl)-1'H-spiro[cyclopropane-1,2'-indolin]-3'-one;
1'-(N,N-Dimethylcarbamoyl)-5'-methoxy-1'H-spiro[cyclopropane-1,2'-indolin]-3'-one;

1'-(2-Bromopropionyl)-5'-methoxy-1'H-spiro[cyclopropane-1,2'-indolin]-3'-one;

1'-(2-Dimethylaminopropionyl)-5'-methoxy-1'H-spiro[cyclopropane-1,2'-indolin]-3'-one;

1'-Mesyl-5'-methoxy-1'H-sprio[cyclopropane-1,2'-indolin]-3'-one;

5'-Methoxy-1'-tosyl-1'H-spiro[cyclopropane-1,2'-indolin]-3'-one;

5'-Methoxy-1'-methyl-1'H-spiro[cyclopropane-1,2'-indolin]-3'-one;

1'-Ethyl-5'-methoxy-1'H-spiro[cyclopropane-1,2'-indolin]-3'-one;

5'-Methoxy-1'-n-propyl-1'H-spiro[cyclopropane-1,2'-indolin]-3'-one;

5'-Methoxy-1'-isopropyl-1'H-spiro[cyclopropane-1,2'-indolin]-3'-one;

1'-Ethoxycarbonylmethyl-5'-methoxy-1'H-spiro[cyclopropane-1,2'-indolin]-3'-one;

5'-Methoxy-1'-phenethyl-1'H-spiro[cyclopropane-1,2'-indolin]-3'-one;

1'-Benzyl-5'-methoxy-1'H-sprio[cyclopropane-1,2'-indolin]-3'-one

The numbering of the spiro[cyclopropane-1,2'-indolin]-3'-ones and 4,5-dihydrospiro[furan-3(3H), 2'-indoline]-2,3'-dione is shown below.

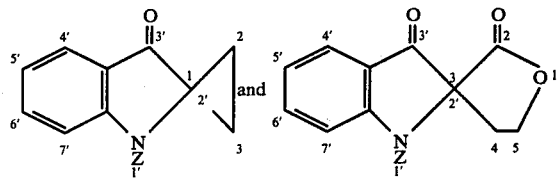

Throughout the specifications and claims alkyl groups and alkyl parts of the groups containing alkyls, e.g. alkoxy groups, alkyl cargonyl groups or mono- or di-alkyl amino groups, etc. may be straight or branched.

EXAMPLE 1

In 100 ml of dimethyl sulfoxide was dissolved 12.2 g of 4,5-dihydro-1'H-spiro[furan-3(3H), 2'-indoline]-2,3'-dione, followed by the addition of 3.86 g of sodium chloride. The reaction was conducted at 160° C for 5 hours under argon sparging. After cooling, ice-water was added to the reaction mixture which was then extracted with chloroform. The chloroform extract was washed with water and dried over magnesium sulfate. The chloroform was distilled off and the residue was purified by column chromatography on silica gel. By the above procedure was obtained 8.91 g of 1'H-spiro[cyclopropane-1,2'-indolin]-3'-one, melting point: 110°–111° C.

Elemental analysis, for $C_{10}H_9NO$

|  | C | H | N |
| --- | --- | --- | --- |
| Calcd. | 75.45 | 5.70 | 8.80 |
| Found | 75.23 | 5.49 | 8.54 |

EXAMPLE 2

In 50 ml of dimethyl sulfoxide was dissolved 6.1 g of 4,5-dihydro-1'H-spiro[furan-3(3H), 2'-indoline]-2,3'-dione, followed by the addition of 3.4 g of sodium bromide. Under argon sparging, the reaction was conducted at 160° C for 1.5 hours. Then, the reaction mixture was treated in the same manner as Example 1 to obtain 4.26 g of 1'H-spiro[cyclopropane-1,2'-indolin]-3'-one. This 1'H-spiro[cyclopropane-1,2'-indolin]-3'-one was in complete agreement with the product of Example 1 in melting point and elemental analysis.

EXAMPLE 3

In 2 ml of dimethyl sulfoxide was dissolved 0.491 g of 1'-acetyl-4,5-dihydro-1'H-spiro[furan-3(3H), 2'-indoline]-2,3'-dione and, then, 0.129 g of sodium chloride was added. Under nitrogen sparging, the reaction was conducted at 155°–160° C for 2 hours. After cooling, ice-water was added to the reaction mixture which was then extracted with chloroform. The extract was washed with water and dried over magnesium sulfate. The chloroform was distilled off and the residue was purified by column chromatography on silica gel. By the above procedure was obtained 0.38 g of 1'-acetyl-1'H-spiro[cyclopropane-1,2'-indolin]-3'-one. Recrystallized from ethanol, the crystals melted at 156°–157° C.

Elemental analysis, for $C_{12}H_{11}NO_2$

|  | C | H | N |
| --- | --- | --- | --- |
| Calcd. | 71.62 | 5.51 | 6.96 |
| Found | 71.33 | 5.55 | 6.68 |

EXAMPLE 4

In 6.5 ml of diemthyl sulfoxide was dissolved 1.503 g of 1'-formyl-4,5-dihydro-1'H-spiro[furan-3(3H), 2'-indoline]-2,3'-dione, and 0.736 g of sodium bromide was added. Under argon sparging, the reaction was conducted at 150° C for 2 hours. After cooling, ice-water was added, followed by extraction with chloroform. The extract was washed with water and dried over magnesium sulfate. The chlorofrom was distilled off and the residue was purified by column chromatography on silica gel. By the above procedure was obtained 1.102 g of 1'-formyl-1'H-spiro[cyclopropane-1,2'-indolin]-3'-one. Recrystallized from ethanol, the compound melted at 122°–123° C.

Elemental analysis, for $C_{11}H_9NO_2$

|  | C | H | N |
| --- | --- | --- | --- |
| Calcd. | 70.58 | 4.85 | 7.48 |
| Found | 70.63 | 4.89 | 7.33 |

EXAMPLE 5

In 5 ml of dimethyl sulfoxide was dissolved 0.684 g of 1'-(4-chlorobenzoyl)-4,5-dihydro-1'H-spiro[furan-3(3H), 2'-indoline]-2,3'-dione, followed by the addition of 0.227 g of sodium bromide.

Under argon sparging, the reaction was conducted at 160° C for 1 hour. After cooling, ice-water was added to the reaction mixture which was then extracted with chloroform. The extract was washed with water and dried over magnesium sulfate. The chloroform was distilled off and the residue was purified by column chromatography on silica gel. By the above procedure was obtained 0.511 g of 1'-(4-chlorobenzoyl)-1'H-spiro[cyclopropane-1,2'-indolin]-3'-one. Recrystallized from ethanol, the product melted at 118°–119° C.

Elemental analysis, for $C_{17}H_{12}NO_2Cl$

|  | C | H | N |
| --- | --- | --- | --- |
| Calcd. | 68.58 | 4.06 | 4.70 |

|       | C     | H    | N    |
|-------|-------|------|------|
| Found | 68.74 | 4.10 | 4.39 |

EXAMPLE 6

In 1.5 ml of dimethyl sulfoxide was dissolved 0.435 g of 4,5-dihydro-1'-methyl-1'H-spiro[furan-3(3H),2'-indoline]-2,3'-dione, followed by the addition of 0.129 g of sodium chloride. Under nitrogen sparging, the reaction was conducted at 150°–155° C for 3 hours. After cooling, ice-water was added to the reaction mixture which was then extracted with chloroform. The extract was washed with water and dried over magnesium sulfate. The chloroform was distilled off and the residue was purified by column chromatography on silica gel. By the above procedure was obtained 0.31 g of 1'-methyl-1'H-spiro[cyclopropane-1,2'-indolin]-3'-one. Recrystallized from diisopropyl ether, the product melted at 73°–75° C.

Elemental analysis, for $C_{11}H_{11}NO$

|        | C     | H    | N    |
|--------|-------|------|------|
| Calcd. | 76.27 | 6.40 | 8.09 |
| Found  | 76.45 | 6.19 | 8.15 |

EXAMPLE 7

In 5 ml of dimethyl sulfoxide was dissolved 0.551 g of 1'-acetyl-4,5-dihydro-5'-methoxy-1'H-spiro[furan-3(3H), 2'-indoline]-2,3'-dione, followed by the addition of 0.129 g of sodium chloride. Under argon sparging, the reaction was conducted at 160° C for 3 hours. After cooling, ice-water was added to the reaction mixture which was then extracted with chloroform. The extract was washed with water and dried over magnesium sulfate. The chloroform was distilled off and the residue was purified by column chromatography on silica gel. By the above procedure was obtained 0.396 g of 1'-acetyl-5'-methoxy-1'H-spiro[cyclopropane-1,2'-indolin]-3'-one. Recrystallized from ethanol, the compound melted at 169°–172° C.

Elemental analysis, for $C_{13}H_{13}NO_3$

|        | C     | H    | N    |
|--------|-------|------|------|
| Calcd. | 67.52 | 5.67 | 6.06 |
| Found  | 67.61 | 5.55 | 6.05 |

EXAMPLE 8

In 10 ml of dimethyl sulfoxide was dissolved 1.22 g of 1'-acetyl-4,5-dihydro-5',6'-dimethoxy-1'H-spiro[furan-3(3H), 2'-indoline]-2,3'-dione, followed by the addition of 0.257 g of sodium chloride. Under argon sparging, the reaction was conducted at 160° C for 3.5 hours. After cooling, ice-water was added to the reaction mixture which was then extracted with chloroform. The extract was washed with water and dried over magnesium sulfate. The chloroform was distilled off and the residue was purified by column chromatography on silica gel. By the above procedure was obtained 0.79 g of 1'-acetyl-5',6'-dimethoxy-1'H-spiro[cyclopropane-1,2'-indolin]-3'-one. Recrystallized from ethanol. Melting point: 174°–176° C.

Elemental analysis, for $C_{14}H_{15}NO_4$

|        | C     | H    | N    |
|--------|-------|------|------|
| Calcd. | 64.36 | 5.79 | 5.36 |
| Found  | 64.36 | 5.74 | 5.32 |

EXAMPLE 9

In 30 ml of dimethyl sulfoxide was dissolved 2.52 g of 1'-acetyl-5'-chloro-4,5-dihydro-1'H-spiro[furan-3(3H), 2'-indoline]-2,3'-dione, followed by the addition of 0.58 g of sodium chloride. Under argon sparging, the reaction was conducted at 155° C for 1 hour. After cooling, ice-water was added to the reaction mixture and the resulting crystals were recovered by filtration, rinsed well with water and dried. By the above procedure was obtained 2.02 g of 1'-acetyl-5'-chloro-1'H-spiro[cyclopropane-1,2'-indolin]-3'-one. Recrystallized from ethanol. Melting point: 188°–189° C.

Elemental analysis, for $C_{12}H_{10}NO_2Cl$

|        | C     | H    | N    |
|--------|-------|------|------|
| Calcd. | 61.15 | 4.28 | 5.94 |
| Found  | 61.18 | 4.31 | 6.16 |

EXAMPLE 10

In 21 ml of 99% formic acid was dissolved 1.12 g of 1'H-spiro[cyclopropane-1,2'-indolin]-3'-one and, under ice-cooling and stirring, 7 ml of acetic anhydride was added. The mixture was stirred under ice-cooling for 1 hour and at room temperature for 4 hours, after which time ice-water was added. The mixture was extracted with chloroform and the extract was washed with water and dried over magnesium sulfate. The chloroform was distilled off and the residue was purified by column chromatography on silica gel. By the above procedure was obtained 1.027 g of 1'-formyl-1'H-spiro[cyclopropane-1,2'-indolin]-3'-one. Recrystallized from ethanol. Mellting point: 122°–123° C. In elemental analysis, infrared absorption spectrum and other properties, this 1'-formyl-1'H-spiro[cyclopropane-1,2'-indolin]-3'-one was in complete agreement with the compound obtained in Example 4.

EXAMPLE 11

In 5 ml of dry pyridine was dissolved 0.319 g of 1'H-spiro[cyclopropane-1,2'-indolin]-3'-one and, under ice-cooling and stirring, 0.525 g of 4-chlorobenzoyl chloride was added. The mixture was stirred at room temperature for 1.5 hours. Following the addition of ice-water, the reaction mixture was extracted with ethyl acetate and the extract was washed with water and dried over magnesium sulfate. The ethyl acetate was distilled off and the residue was purified by column chromatography on silica gel. By the above procedure was obtained 0.279 g of 1'-(4-chlorobenzoyl)-1'H-spiro[cyclopropane-1,2'-indolin]-3'-one. In melting point, elemental analysis, infrared absorption spectrum, this 1'-(4-chlorobenzoyl)-1'H-spiro[cyclopropane-1,2'-indolin]-3'-one was in complete agreement with the product compound according to Example 5.

EXAMPLE 12

Under argon sparging, while a mixture of 0.144 g of 50% (weight/volume) sodium hydride in oil and 5 ml of dry dimethyl sulfoxide was stirred under ice-cooling, a solution of 0.319 g of 1'H-spiro[cyclopropane-1,2'-indolin]-3'-one in 3 ml of dry dimethyl sulfoxide was added. The mixture was stirred at room temperature for 30 minutes and, then, under ice-cooling and stirring again, a solution of 0.47 g of 4-methoxybenzyl chloride in 3 ml of dry dimethyl sulfoxide was added. The mixture was then stirred at room temperature for 1 hour. Ice-water was added to the reaction mixture which was then extracted with chloroform. The extract was washed with water and dried over magnesium sulfate. The chloroform was distilled off and the residue was purified by column chromatography on silica gel. By the above procedure was obtained 0.57 g of 1'-(4-methoxybenzyl)-1'H-spiro[cyclopropane-1,2'-indolin]-3'-one. Recrystallized from diisopropyl ether. Melting point: 66°-67° C.

Elemental analysis, for $C_{18}H_{17}NO_2$

|  | C | H | N |
|---|---|---|---|
| Calcd. | 77.39 | 6.13 | 5.01 |
| Found | 77.13 | 6.15 | 4.92 |

EXAMPLE 13

In nitrogen streams, while a mixture of 0.144 g of 50% (weight/volume) sodium hydride in oil and 5 ml of dry dimethyl sulfoxide was stirred under ice-cooling, a solution of 0.319 g of 1'H-spiro[cyclopropane-1,2'-indolin]-3'-one in 3 ml of dry dimethyl sulfoxide was added. The mixture was stirred at room temperature for 20 minutes and, then, a solution of 0.487 g of 3-dimethylaminopropyl chloride in 3 ml of dry dimethyl sulfoxide was added. The mixture was reacted with stirring at room temperature for 30 minutes and, then, at 50° C for 75 minutes. Ice-water was added to the reaction mixture which was then extracted with chloroform. The extract was washed with water and dried over magnesium sulfate. The chloroform was distilled off and the residue was purified by column chromatography on alumina. By the above procedure was obtained 0.58 g of 1'-(3-dimethylaminopropyl)-1'H-spiro[cyclopropane-1,2'-indolin]-3'-one as an oil. This product was dissolved in 5 ml of ethanol, followed by the addition of a solution of 0.18 g of oxalic acid in 5 ml of ethanol. The resulting crystals were recovered by filtration, washed with ethanol and dried. By the above procedure was obtained 0.505 g of 1'-(3-dimethylaminopropyl)-1'H-spiro[cyclopropane-1,2'-indolin]-3'-one oxalate (1:1). Recrystallized from ethanol. Melting point: 173°-174° C(decomp.)

Elemental analysis, for $C_{17}H_{22}N_2O_5$

|  | C | H | N |
|---|---|---|---|
| Calcd. | 61.06 | 6.63 | 8.38 |
| Found | 60.93 | 6.70 | 8.45 |

EXAMPLE 14

In nitrogen streams, while a mixture of 0.144 g of 50% (weight/volume) sodium hydride in oil and 5 ml of dry dimethyl sulfoxide was stirred under ice-cooling, a solution of 0.319 g of 1'H-spiro[cyclopropane-1,2'-indolin]-3'-one in 3 ml of dry dimethyl sulfoxide was added. The mixture was stirred at room temperature for 30 minutes and, then, under stirring and ice-cooling again, a solution of 0.735 g of 4'-chloro-4-fluorobutyrophenone ethylene acetal in 3ml of dry dimethyl sulfoxide was added. The mixture was reacted with stirring at room temperature for 2 hours and, then, at 50°-55° C for 5 hours. Ice-water was added to the reaction mixture which was then extracted with chloroform. The extract was washed with water and dried over magnesium sulfate. The chloroform was distilled off and the residue was purified by column chromatography on silica gel. By the above procedure was obtained 0.734 g of 1'-[3-(4-fluorobenzoyl)propyl]-1'H-spiro[cyclopropane-1,2'-indolin]-3'-one ethylene acetal. Recrystallized from diisopropyl ether. Melting point: 96°-97° C.

Elemental analysis, for $C_{22}H_{22}NO_3F$

|  | C | H | N |
|---|---|---|---|
| Calcd. | 71.92 | 6.04 | 3.81 |
| Found | 71.88 | 6.09 | 3.85 |

In 100 ml of ethanol was dissolved 1.47 g of the 1'-[3-(4-fluorobenzoyl)propyl]-1'H-spiro[cyclopropane-1,2'-indolin]-3'-one ethylene aectal obtained as above and, under ice-cooling and stirring, a solution consisting of 25 g of 85% (weight/volume) phosphoric acid in water and 25 g of water was added. The mixture was stirred under ice-cooling for 3 hours and, then, at room temperature for 10 hours. The reaction mixture was concentrated under reduced pressure and ice-water was added to the residue which which was then extracted with chloroform. The extract was washed with water and dried over magnesium sulfate. The chloroform was distilled off and the residue was purified by column chromatography on silica gel. By the above procedure was obtained 1.25 g of 1'-[3-(4-fluorobenzoyl)-propyl]-1'H-spiro[cyclopropane-1,2'-indolin]-3'-one. Recrystallized from diisopropyl ether. Melting point: 87.5°-88.5° C.

Elemental analysis, for $C_{20}H_{18}NO_2F$

|  | C | H | N |
|---|---|---|---|
| Calcd. | 74.28 | 5.61 | 4.33 |
| Found | 74.89 | 5.47 | 4.33 |

EXAMPLE 15

In argon gas streams, while a mixture of 0.144 g of 50% (weight/volume) sodium hydride in oil and 5 ml of dry dimethyl sulfoxide was stirred under ice-cooling, a solution of 0.319 g of 1'H-spiro[cyclopropane-1,2'-indolin]-3'-one in 3 ml of dry dimethyl sulfoxide was added. The mixture was stirred at room temperature for 20 minutes, after which time a solution of 0.536 g of 2-(3-chloropropoxy)tetrahydropyran in 3 ml of dry dimethyl sulfoxide was added. The mixture was stirred at room temperature for 2 hours and, then, at 50° C for 1.5 hours. Ice-water was added to the reaction mixture which was then extracted with chloroform. The chloroform was distilled off and the residue was purified by column chromatography on silica gel. By the above procedure was obtained 0.576 g of 1'-[3-(2-tetrahydropyranyloxy)propyl]-1'H-spiro[cyclopropane-1,2'-indolin]-3'-one. In 7 ml of methanol was dissolved 0.302 g of this 1'-[3-(2-tetrahydropyranyloxy)propyl]-1'H-spiro[cyclopropane-1,2'-indolin]-3'-one and, after the addition of 3 ml of acetic acid, the solution was refluxed for 5 hours. The reaction mixture was concentrated under reduced pressure and the resulting residue was purified by column chromatography on silica gel. By the above procedure was obtained 0.12 g of 1'-(3-hydroxypropyl)-1'H-spiro[cyclopropane-1,2'-indolin]-3'-one as an oil.
Infrared absorption spectrum (liquid film) 3400cm$^{-1}$(hydroxy), 1670cm$^{-1}$(ketone)

EXAMPLE 16

Under argon sparging, while a mixture of 0.72 g of 50% (weight/volume) sodium hydride in oil and 15 ml of dry dimethyl sulfoxide was stirred under ice-cooling, a solution of 1.59 g of 1'H-spiro[cyclopropane-1,2'-indolin]-3'-one in 15 ml of dry dimethyl sulfoxide was added. The mixture was stirred at room temperature for 1 hour and, then, under stirring and ice-cooling, a solution of 2.505 g of ethyl bromoacetate in 10 ml of dry dimethyl sulfoxide was added. The mixture was then stirred at room temperature for 5 hours. Ice-water was added to the reaction mixture, which was then extracted with chloroform. The extract was washed with water and dried over magnesium sulfate. The chloroform was distilled off and the residue was purified by column chromatography on silica gel. By the above procedure was obtained 1.98 g of 1'-ethoxycarbonylmethyl-1'H-spiro[cyclopropane-1,2'-indolin]-3'-one.
Infrared absorption spectrum (Nujol) 1735 cm$^{-1}$(ester), 1689 cm$^{-1}$(ketone)

In 10 ml of methanol was dissolved 0.491 g of the above 1'-ethoxycarbonylmethyl-1'H-spiro[cyclopropane-1,2'-indolin]-3'-one and, under ice-cooling and stirring, 2 ml of a 10% (weight/weight) aqueous solution of potassium hydroxide was added. The mixture was stirred at room temperature for 2 hours. Then, the reaction mixture was concentrated under reduced pressure and a small amount of water was added to the concentrate. Under ice-cooling, the solution was made acidic with 1N-hydrochloric acid. The resulting crystals were recovered by filtration, rinsed with water and recrystallized from 50% (volume/volume) aqueous ethanol. By the above procedure was obtained 0.413 g of 1'-carboxylmethyl-1'H-spiro[cyclopropane-1,2'-indolin]-3'-one monohydrate, melting point: 154° C(decomp.).
Elemental analysis, for $C_{12}H_{13}NO_4$

|  | C | H | N |
|---|---|---|---|
| Calcd. | 61.27 | 5.57 | 5.96 |
| Found | 61.53 | 5.32 | 5.93 |

EXAMPLE 17

While 9.9 ml of 30% (weight/volume) solution of phosgene in carbon tetrachloride and 30 ml of carbon tetrachloride were stirred under ice-cooling, a solution of 2.39 g of 1'H-spiro[cyclopropane-1,2'-indolin]-3'-one and 1.897 g of triethylamine in 50 ml of dry benzene was added. The mixture was stirred at room temperature for 2 hours, after which time it was concentrated under reduced pressure. To the residue was added 100 ml of dry benzene and, under ice-cooling and stirring, ammonia gas was passed through the solution for 1 hour. The benzene was distilled off under reduced pressure and to the residue was added water. The residue was extracted with chloroform. The extract was washed with water and dried over magnesium sulfate. The chloroform was distilled off and the crystalline residue was treated with ethanol and recovered by filtration. The crystals were rinsed with ethanol and dried. By the above procedure was obtained 2.25 g of 1'-carbamoyl-1'H-spiro-[cyclopropane-1,2'-indolin]-3'-one. Recrystallized from ethanol. Melting point: 210°–212° C(decomp.)
Elemental analysis, for $C_{11}H_{10}N_2O_2$

|  | C | H | N |
|---|---|---|---|
| Calcd. | 65.33 | 4.98 | 13.86 |
| Found | 65.03 | 4.91 | 13.82 |

EXAMPLE 18

In 10 ml of dry benzene was dissolved 0.478 g of 1'H-spiro[cyclopropane-1,2'-indolin]-3'-one, followed by the addition of 0.343 g of methyl isocyanate. The mixture was stirred at room temperature for 3 hours and, then, refluxed for 6.5 hours. Following a further addition of 0.343 g of methyl isocyanate, the mixture was refluxed for another 18 hours. The reaction mixture was concentrated under reduced pressure and the residue was purified by column chromatography on silica gel. By the above procedure was obtained 0.616 g of 1'-(N-methylcarbamoyl)-1'H-spiro[cyclopropane-1,2'-indolin]-3'-one. Recrystallized from methanol. Melting point: 115°–116° C.
Elemental analysis, for $C_{12}H_{12}N_2O_2$

|  | C | H | N |
|---|---|---|---|
| Calcd. | 66.65 | 5.59 | 12.96 |
| Found | 66.40 | 5.54 | 12.82 |

EXAMPLE 19

In 40 ml of dimethyl sulfoxide was dissolved 9.08 g of 1'-acetyl-4,5-dihydro-5'-methyl-1'H-spiro[furan-3(3H),2'-indoline]-2,3'-dione, followed by the addition of 2.25 g of sodium chloride. Under nitrogen sparging, the reaction was conducted at 155° C for 2 hours. After cooling, ice-water was added to the reaction mixture and the resultant crystals were recovered by filtration, washed with water and recrystallized from ethanol. By the above procedure was obtained 6.55 g of 1'-acetyl-5'-methyl-1'H-spiro[cyclopropane-1,2'-indolin]-3'-one, melting point: 137°–138° C.
Elemental analysis, for $C_{13}H_{13}NO_2$

|  | C | H | N |
|---|---|---|---|
| Calcd. | 72.54 | 6.09 | 6.51 |
| Found | 72.86 | 6.29 | 6.53 |

EXAMPLE 20

In 12 ml of dimethyl sulfoxide was dissolved 3.12 g of 4,5-dihydro-1'-propionyl-1'H-spiro[furan-3(3H),2'-indoline]-2,3'-dione, followed by the addition of 0.78 g of sodium chloride. Under nitrogren sparging, the reaction was conducted at 155°–160° C for 2 hours. After cooling, ice-water was added to the reaction mixture and the resultant crystals were recovered by filtration, washed with water and recrystallized from ethanol. By the above procedure was obtained 2.008 g of 1'-propionyl-1'H-sprio[cyclopropane-1,2'-indolin]-3'-one, melting point: 172.5°–173.5° C.
Elemental analysis, for $C_{13}H_{13}NO_2$

|  | C | H | N |
|---|---|---|---|
| Calcd. | 72.54 | 6.09 | 6.51 |
| Found | 72.68 | 6.11 | 6.41 |

EXAMPLE 21

In 40 ml of chloroform was dissolved 1.91 g of 1'H-spiro[cyclopropane-1,2'-indolin]-3'-one, followed by the addition of 3.65 g of triethylamine. Under ice-cooling and stirring, a solution of 3.84 g of isobutyryl chloride in 20 ml of chloroform was added dropwise over a period of 40 minutes. The mixture was stirred under ice-cooling for 40 minutes and, then, at room temperature for 2 hours. Then, it was left standing overnight. Ice-water was added to the reaction mixture and the chloroform layer was separated. The water layer was extracted twice with chloroform. The chloroform extracts were combined, washed with water and dried over magnesium sulfate. The chloroform was distilled off and the residue was purified by column chromatography on silica gel. By the above procedure was obtained 1.068 g of 1'-isobutyryl-1'H-spiro[cyclopropane-1,2'-indolin]-3'-one. Recrystallized from ethanol, melting point: 90°–91° C.

Elemental analysis, for $C_{14}H_{15}NO_2$

|  | C | H | N |
|---|---|---|---|
| Calcd. | 73.34 | 6.59 | 6.11 |
| Found | 73.29 | 6.56 | 6.02 |

EXAMPLE 22

In 30 ml of chloroform was dissolved 1.12 g of 1'H-spiro[cyclopropane-1,2'-indolin]-3'-one, followed by the addition of 3.78 g of triethylamine. Under ice-cooling and stirring, a solution of 3.17 g of chloroacetyl chloride in 20 ml of chloroform was added dropwise over a period of 30 minutes. The mixture was stirred under ice-cooling for 30 minutes, at the end of which time ice-water was added. The chloroform layer was separated and the water layer was extracted twice with chloroform. The chloroform extracts were combined, washed with water and dried over magnesium sulfate. The chloroform extract was concentrated until its total volume was about 50 ml, and dimethylamine gas was passed through the residue for 20 minutes. The mixture was then stirred at room temperature for 1.5 hours, at the end of which time ice-water was added. The chloroform layer was taken and the water layer was extracted twice with chloroform. The chloroform extracts were combined, washed with water and dried over magnesium sulfate. The chloroform was distilled off and the residue was dissolved in 30 ml of ethyl acetate, followed by the addition of a solution of 0.813 g of maleic acid in 30 ml of ethyl acetate. The resulting crystals were recovered by filtration. By the above procedure was obtained 2.30 g of 1'-dimethyl-aminoacetyl-1'H-spiro[cyclopropane-1,2'-indolin]-3'-one maleate (1:1). Recrystallized from ethanol, melting point: 162.5°–163.5° C(decomp.).

Elemental analysis, for $C_{18}H_{20}N_2O_6$

|  | C | H | N |
|---|---|---|---|
| Calcd. | 59.99 | 5.59 | 7.77 |
| Found | 59.74 | 5.66 | 7.71 |

EXAMPLE 23

1'-Chloroacetyl-1'H-spiro[cyclopropane-1,2'-indolin]-3'-one synthesized on the same scale and by the same procedure as in Example 22 was dissolved in 50 ml of chloroform and while this solution was stirred at room temperature, a solution of 5.96 g of piperidine in 20 ml of chloroform was added dropwise over a period of 20 minutes. The mixture was allowed to stand overnight and, then, ice-water was added. The chloroform layer was taken and the water layer was extracted twice with chloroform. The chloroform extracts were combined, washed with water and dried over magnesium sulfate. The chloroform was distilled off and the residue was purified by column chromatography on silica gel. The resulting crystals of 1'-piperidinoacetyl-1'H-spiro[cyclopropane-1,2'-indolin]-3'-one were dissolved in 20 ml of ethyl acetate, followed by the addition of a solution of 0.557 g of maleic acid in 30 ml of ethyl acetate. The resulting crystals were recovered by filtration. By the above procedure was obtained 2.038 g of 1'-piperidinoacetyl-1'H-spiro[cyclopropane-1,2'-indolin]-3'-one maleate (1:1). Recrystallized from ethanol, melting point: 148°–149° C.

Elemental analysis, for $C_{21}H_{24}N_2O_6$

|  | C | H | N |
|---|---|---|---|
| Calcd. | 62.99 | 6.04 | 7.00 |
| Found | 62.33 | 6.00 | 6.80 |

EXAMPLE 24

In 50 ml of chloroform was dissolved 1.59 g of 1'H-spiro[cyclopropane-1,2'-indolin]-3'-one, followed by the addition of 8.1 g of triethylamine. Under ice-cooling and stirring, a solution of 13.0 g of 2-bromopropionyl bromide in 50 ml of chloroform was added dropwise over a period of 40 minutes. The mixture was stirred under ice-cooling for 1 hour and, then, at room temperature for 1 hour, after which time ice-water was added. The chloroform layer was taken and the water layer was extracted twice with chloroform. The chloroform extracts were combined, washed with water and dried over magnesium sulfate. The chloroform solution was concentrated to about 100 ml and, under ice-cooling, dimethylamine gas was passed through the residue for 40 minutes. The residue was then stirred at room temperature for 1 hour, after which time the chloroform was distilled off. Ice-water was added to the residue, which was extracted 3 times with ethyl acetate. The ethyl acetate extract was washed once with water and once with a saturated aqueous solution of sodium chloride, followed by drying over magnesium sulfate. The ethyl acetate was distilled off and the residue was purified by column chromatography on silica gel. The resulting 1'-(2-dimethylaminopropionyl)-1'H-spiro[cyclopropane-1,2'-indolin]-3'-one was dissolved in 30 ml of ethyl acetate, followed by the addition of a solution of 1.16 g of maleic acid in 50 ml of ethyl acetate. The resulting crystals were recovered by filtration. By the above procedure was obtained 2.49 g of 1'-(2-dimethylamino-propionyl)-1'H-spiro[cyclopropane-1,2'- indolin]-3'-one maleate (1:1). Recrystallized from ethanol, melting point: 160°–161° C(decomp.).
Elemental analysis, for $C_{19}H_{22}N_2O_6$

|  | C | H | N |
|---|---|---|---|
| Calcd. | 60.95 | 5.92 | 7.48 |
| Found | 60.91 | 6.00 | 7.54 |

EXAMPLE 25

In 15 ml of dry tetrahydrofuran was dissolved 0.478 g of 1'H-spiro[cyclopropane-1,2'-indolin]-3'-one and, under argon sparging, the solution was cooled to −70° C, followed by the addition of 1.92 ml of n-butyllithium (15%(weight/volume) in hexane). The mixture was stirred for 5 minutes, after which time a solution of 0.651 g of ethyl chlorocarbonate in 5 ml of dry tetrahydrofuran was added, followed by stirring at −70° C for 30 minutes. Water was added to the reaction mixture which was then extracted with ethyl acetate. The extract was washed once with water and once with a saturated aqueous solution of sodium chloride, followed by drying over magnesium sulfate. The ethyl acetate was distilled off and the residue was purified by column chromatography on silica gel. By the above procedure was obtained 0.565 g of 1'-ethoxycarbonyl-1'H-spiro[cyclopropane-1,2'-indolin]-3'-one. Recrystallized from cyclohexane, melting point: 87.5°–88.5° C.
Elemental analysis, for $C_{13}H_{13}NO_3$

|  | C | H | N |
|---|---|---|---|
| Calcd. | 67.52 | 5.67 | 6.06 |
| Found | 67.43 | 5.63 | 5.92 |

EXAMPLE 26

In 5 ml of pyridine was dissolved 0.478 g of 1'H-spiro[cyclopropane-1,2'-indolin]-3'-one, followed by the addition of a solution of 0.688 g of methanesulfonyl chloride in 3 ml of pyridine. The mixture was stirred at room temperature for 6 hours and, then, allowed to stand for 2 days. Ice-water was added to the reaction mixture, which was then extracted withe ethyl acetate. The extract was washed twice with water and once with a saturated aqueous solution of sodium chloride, followed by drying over magnesium sulfate. The ethyl acetate was distilled off and the residue was purified by column chromatography on silica gel. By the above procedure was obtained 0.64 g of 1'-mesyl-1'H-spiro[cyclopropane-1,2'-indolin]-3'-pne. Recrystallized from ethanol. Melting point: 142°–143° C.
Elemental analysis, for $C_{11}H_{11}NO_3S$

|  | C | H | N |
|---|---|---|---|
| Calcd. | 55.69 | 4.67 | 5.91 |
| Found | 55.59 | 4.69 | 5.88 |

EXAMPLE 27

In 15 ml of pyridine was dissolved 1.44 g of 1'H-spiro[cyclopropane-1,2'-indolin]-3'-one, followed by the addition of a solution of 2.58 g of p-toluenesulfonyl chloride in 9 ml of pyridine. The mixture was allowed to stand for 2 days. Ice-water was added to the reaction mixture which was extracted with ethyl acetate. The extract was washed twice with water and once with a saturated aqueous solution of sodium chloride, followed by drying over magnesium sulfate. The ethyl acetate was distilled off and the residue was purified by column chromatography on silica gel. By the above procedure was obtained 2.5 g of 1'-tosyl-1'H-spiro[cyclopropane-1,2'-indolin]-3'-one. Recrystallized from methanol, melting point: 125°–126° C.
Elemental analysis, for $C_{17}H_{15}NO_3S$

|  | C | H | N |
|---|---|---|---|
| Calcd. | 65.17 | 4.82 | 4.47 |
| Found | 65.37 | 4.64 | 4.31 |

EXAMPLE 28

Under argon sparging, while a mixture of 0.576 g of 50% (weight/volume) sodium hydride in oil and 10 ml of dry dimethyl sulfoxide was stirred at room temperature, a solution of 0.478 g of 1'H-spiro[cyclopropane-1,2'-indolin]-3'-one in 5 ml of dry dimethyl sulfoxide was added. The mixture was stirred at room temperature for 30 minutes, at the end of which time a suspension of 0.865 g of 2-dimethylaminoethyl chloride hydrochloride in 5 ml of dry dimethyl sulfoxide was added. The mixture was stirred at room temperature for 30 minutes and, then, at 50° C for 1 hour. Ice-water was added to the reaction mixture, which was then extracted with chloroform. The extract was washed with water and dried over magnesium sulfate. The chloroform was distilled off and the residue was dissolved in 30 ml of ethanol, followed by the addition of a solution of 0.27 g of oxalic acid in 30 ml of ethanol. The resulting crystals were recovered by filtration and washed with ethanol and ethyl ether. By the above procedure was obtained 0.795 g of 1'-(2-dimethylaminoethyl)-1'H-spiro[cyclopropane-1,2'-indolin]-3'-one oxalate (1:1). Recrystallized from 95% aqueous ethanol, melting point: 183° C(decomp.)
Elemental analysis, for $C_{16}H_{20}N_2O_5$

|  | C | H | N |
|---|---|---|---|
| Calcd. | 59.99 | 6.29 | 8.75 |
| Found | 59.83 | 6.35 | 8.96 |

EXAMPLE 29

Under argon sparging, while a mixture of 1.16 g of 50% (weight/volume) sodium hydride in oil and 20 ml of dry dimethyl sulfoxide was stirred at room temperature, a solution of 1.28 g of 1'H-spiro[cyclopropane-1,2'-indolin]-3'-one in 10 ml of dry dimethyl sulfoxide was added. The mixture was stirred at room temperature for 30 minutes, at the end of which time 2.07 g of 2-diethylaminoethyl chloride hydrochloride was added. The mixture was further stirred at room temperature for 3 hours. Ice-water was added to the reaction mixture, which was then extracted with ethyl acetate. The extract was washed with water and dried over magnesium sulfate. The ethyl acetate was distilled off and the residue was dissolved in 40 ml of ethanol. To this was added a solution of 0.72 g of oxalic acid in 40 ml of ethanol. The resulting crystals were recovered by filtration and washed with ethanol and ethyl ether. By the above procedure was obtained 2.14 g of 1'-(2-diethylaminoethyl)-1'H-spiro[cyclopropane-1,2'-indolin]-

3'-one oxalate (1:1). Recrystallized from ethanol, melting point: 156° C(decomp.).
Elemental analysis, for $C_{18}H_{24}N_2O_5$

|  | C | H | N |
|---|---|---|---|
| Calcd. | 62.05 | 6.94 | 8.04 |
| Found | 61.82 | 6.95 | 8.05 |

EXAMPLE 30

Under argon sparging, while a mixture of 0.216 g of 50% (weight/volume) sodium hydride in oil and 10 ml of dry dimethyl sulfoxide was stirred at room temperature, a solution of 0.478 g of 1'H-spiro[cyclopropane-1,2'-indolin]-3'-one in 10 ml of dry dimethyl sulfoxide was added. The mixture was stirred at room temperature for 20 minutes, at the end of which time a solution of 0.582 g of 2-chloroacetopiperidide in 10 ml of dry dimethyl sulfoxide was added. The mixture was further stirred at room temperature for 1.5 hours. Ice-water was added to the reaction mixture, which was then extracted with ethyl acetate. The extract was washed with water and dried over magnesium sulfate. The ethyl acetate was distilled off and the residue was purified by column chromatography on silica gel. By the above procedure was obtained 0.637 g of 1'-piperidonocarbonylmethyl-1'H-spiro[cyclopropane-1,2'-indolin]-3'-one. Recrystallized from benzene, melting point: 148.5°–149.5° C.
Elemental analysis, for $C_{17}H_{20}N_2O_2$

|  | C | H | N |
|---|---|---|---|
| Calcd. | 71.80 | 7.09 | 9.85 |
| Found | 71.89 | 7.13 | 9.82 |

EXAMPLE 31

In argon streams, while a mixture of 0.216 g of 50% (weight/volume) sodium hydride in oil and 10 ml of dry dimethyl sulfoxide was stirred, a solution of 0.478 g of 1'H-spiro[cyclopropane-1,2'-indolin]-3'-one in 5 ml of dry dimethyl sulfoxide was added. The mixture was stirred at room temperature for 20 minutes and, then, a solution of 0.823 g of isobutyl bromide in 5 ml of dry dimethyl sulfoxide was added. The mixture was stirred at room temperature for 6 hours. Ice-water was added to the reaction mixture which was then extacted with chloroform. The extract was washed with water and dried over magnesium sulfate. The chloroform was distilled off and the residue was purified by column chromatography on silica gel. By the above procedure was obtained 0.351 g of 1'-isobutyl-1'H-spiro[cyclopropane-1,2'-indolin]-3'-one as an oil.
Infrared absorption spectrum (liquid film): 1685cm$^{-1}$(ketone), 1615cm$^{-1}$(aromatic)
NMR(CDCl$_3$, ppm): 0.90(doublet, 6H), 1.20(singlet, 4H), 1.6–2.4 (multiplet, 1H, 2.92(doublet, 2H), 6.6–7.8(multiplet, 4H).

REFERENCE EXAMPLE 1

A mixture of 68.6 g of anthranilic acid, 132.2 g of sodium carbonate and 400 ml of water was stirred at room temperature for 1 hour and, under ice-cooling, 103.2 g of α-bromo-γ-butyrolactone was added dropwise. The mixture was stirred under ice-cooling for 5 hours and, then, at room temperature for 24 hours. The mixture was made acidic with hydrochloric acid, extracted with ethyl acetate, washed with water and dried over magnesium sulfate. The ethyl acetate was distilled off and ethyl ether was added to the residue. The resulting crystals were recovered by filtration. By the above procedure was obtained α-[(2-carboxyphenyl)amino]-γ-butyrolactone, melting point: 197°–198° C.
Elemental analysis, for $C_{11}H_{11}NO_4$

|  | C | H | N |
|---|---|---|---|
| Calcd. | 59.72 | 5.01 | 6.33 |
| Found | 59.32 | 4.99 | 6.18 |

REFERENCE EXAMPLE 2

In the method of Reference Example 1, N-methylanthranilic acid was reacted in the place of anthranilic acid to obtain α-[(2-carboxyphenyl)methylamino)-γ-butyrolactone, melting point: 112.5°–114° C.
Elemental analysis, for $C_{12}H_{13}NO_4$

|  | C | H | N |
|---|---|---|---|
| Calcd. | 61.27 | 5.57 | 5.96 |
| Found | 61.37 | 5.59 | 5.85 |

REFERENCE EXAMPLE 3

In the method of the Reference Example 1, 5-methoxyanthranilic acid was reacted in the place of anthranilic acid to obtain α-[(2-carboxy-4-methoxyphenyl)-amino]-γ-butyrolactone, melting point: 206.5°–208° C(decomp.).
Elemental analysis, for $C_{12}H_{13}NO_5$

|  | C | H | N |
|---|---|---|---|
| Calcd. | 57.31 | 5.22 | 5.58 |
| Found | 57.22 | 5.37 | 5.50 |

REFERENCE EXAMPLE 4

In the method of the Reference Example 1,4,5-dimethoxyanthranilic acid was reacted in the place of anthranilic acid to obtain α-[(2-carboxy-4,5-dimethoxyphenyl)-amino]-γ-butyrolactone, melting point: 214° C(decomp.).
Elemental analysis, for $C_{13}H_{15}NO_6$

|  | C | H | N |
|---|---|---|---|
| Calcd. | 55.51 | 5.38 | 4.98 |
| Found | 55.59 | 5.30 | 4.97 |

REFERENCE EXAMPLE 5

In 10 ml of trifluoroacetic anhydride was dissolved 2.22 g of α-[(2-carboxyphenyl)amino]-γ-butyrolactone and the solution was stirred at room temperature for 4 hours. The reaction mixture was concentrated under reduced pressure and to the residue were added 20 ml of acetic anhydride and 4 ml of triethylamine. The resulting mixture was stirred on an oil bath at 115° C for 20 minutes. Ice-water was added to the reaction mixture, which was then extracted with chloroform, washed with water and dried over magnesium sulfate. The chloroform was distilled off and the residue was purified by column chromatography on silica gel. By the above procedure was obtained 4,5-dihydro-1'H-spiro [furan-3(3H),2'-indoline]-2,3'-dione, melting point: 136.5°–137.5° C.
Elemental analysis, for $C_{11}H_9NO_3$

|  | C | H | N |
|---|---|---|---|
| Calcd. | 65.02 | 4.46 | 6.89 |
| Found | 64.68 | 4.33 | 6.81 |

REFERENCE EXAMPLE 6

Under nitrogen sparging, a mixture of 6.64 g of α-[(2-carboxyphenyl)amino]-γ-butyrolactone, 90 ml of acetic anhydride and 18 ml of triethylamine was heated under reflux for 1 hour. The mixture was concentrated under reduced pressure and ice-water was added to the residue. The resulting crystals were recovered by filtration, rinsed well with water and dried. By the above procedure was obtained 6.7 g of 1'-acetyl-4,5-dihydro-1'H-spiro[furan-3(3H),2'-indoline]-2,3'-dione. Recrystallized from ethanol. Melting point: 159°–160° C.
Elemental analysis, for $C_{13}H_{11}NO_4$

|  | C | H | N |
|---|---|---|---|
| Calcd. | 63.67 | 4.52 | 5.71 |
| Found | 63.76 | 4.43 | 5.63 |

REFERENCE EXAMPLE 7

Under nitrogen sparging, a mixture of 0.471 g of α-[(2-carboxyphenyl)methylamino]-γ-butyrolactone, 5 ml of acetic anhydride and 1 ml of triethylamine was heated under reflux for 30 minutes. The reaction mixture was concentrated under reduced pressure and ice-water was added to the residue. The resulting crystals were recovered by filtration, rinsed well with water and dried. By the above procedure was obtained 0.363 g of 4,5-dihydro-1'-methyl-1'H-spiro[furan-3(3H),2'-indolin]-2,3'-dione. Recrystallized from ethanol. Melting point: 184°–185° C.
Elemental analysis, for $C_{12}H_{11}NO_3$

|  | C | H | N |
|---|---|---|---|
| Calcd. | 66.35 | 5.10 | 6.45 |
| Found | 66.38 | 4.71 | 6.30 |

REFERENCE EXAMPLE 8

In the method of the Reference Example 6, α-[(2-carboxy-4-methoxyphenyl)amino]-γ-butyrolactone was reacted in the place of α-[(2-carboxyphenyl)amino]-γ-butyrolactone to obtain 1'-acetyl-4,5-dihydro-5'-methoxy-1'H-spiro[furan-3(3H),2'-indoline]-2,3'-dione, melting point: 136°–138° C.
Elemental analysis, for $C_{14}H_{13}NO_5$

|  | C | H | N |
|---|---|---|---|
| Calcd. | 61.09 | 4.76 | 5.09 |
| Found | 61.13 | 4.66 | 4.96 |

REFERENCE EXAMPLE 9

In the method of the Reference Example 6, α-[(2-carboxy-4,5-dimethoxyphenyl)amino]-α-butyrolactone to obtain 1'-acetyl-4,5-dihydro-5',6'-dimethoxy-1'H-spiro[furan-3(3H), 2'-indoline]-2,3'-dione, melting point: 226°–228° C.
Elemental analysis, for $C_{15}H_{15}NO_6$

|  | C | H | N |
|---|---|---|---|
| Calcd. | 59.01 | 4.95 | 4.59 |
| Found | 58.88 | 4.74 | 4.55 |

REFERENCE EXAMPLE 10

In 9 ml of 99% formic acid was dissolved 0.61 g of 4,5-dihydro-1'H-spiro[furan-3(3H),2'-indoline]-2,3'-dione and, under ice-cooling and stirring, 3 ml of acetic anhydride was added. The mixture was stirred under ice-cooling for 30 minutes and, then, at room temperature for 2 hours. Then, ice-water was added and the resulting crystals were recovered by filtration and rinsed with water. The crude crystals thus obtained were recrystallized from ethanol. By the above procedure was obtained 0.461 g of 1'-formyl-4,5-dihydro-1'H-spiro[furan-3(3H),2'-indoline]-2,3'-dione, melting point: 198.5°–200.5° C.
Elemental analysis, for $C_{12}H_9NO_4$

|  | C | H | N |
|---|---|---|---|
| Calcd. | 62.34 | 3.92 | 6.06 |
| Found | 62.56 | 3.87 | 5.96 |

REFERENCE EXAMPLE 11

A mixture of 0.61 g of 4,5-dihydro-1'H-spiro[furan-3(3H),2'-indoline]-2,3'-dione, 0.375 g of sodium bicarbonate, 1.05 g of 4-chlorobenzoyl chloride, 0.01 g of zinc chloride and 10 ml of chloroform was heated under reflux for 4 hours (after 2 and 3 hours, respectively, 0.01 g of zinc chloride was further added). After cooling, ice-water was added to the reaction mixture, which was then extracted with chloroform. The extract was washed with a saturated aqueous solution of sodium bicarbonate and dried over magnesium sulfate. The chloroform was distilled off and the residue was purified by column chromatography on silica gel. By the above procedure was obtained 0.829 g of 1'-(4-chlorobenzoyl)-4,5-dihydro-1'H-spiro[furan-3(3H), 2'-indoline]-2,3'-dione. Recrystallized from ethanol. Melting point: 151°–152.5° C.
Elemental analysis, for $C_{18}H_{12}NO_4Cl$

|  | C | H | N |
|---|---|---|---|
| Calcd. | 63.26 | 3.54 | 4.10 |
| Found | 63.31 | 3.56 | 4.06 |

REFERENCE EXAMPLE 12

In 150 ml of acetonitrile was dissolved 4.91 g of 1'-acetyl-4,5-dihydro-1'H-spiro[furan-3(3H),2'-indoline]-2,3'-dione and, under ice-cooling, a solution of 80 ml of 3.7% (weight/volume) chlorine in acetonitrile was added dropwise. The mixture was stirred under ice-cooling for 2 hours and, then, at room temperature for 16 hours. The reaction mixture was concentrated under reduced pressure and the residue was recrystallized from ethanol. By the above procedure was obtained 4.2 g of 1'-acetyl-5'-chloro-4,5-dihydro-1'H-spiro[furan- 3(3H),2'-indoline]-2,3'-dione, melting point: 178.5°–180° C.

Elemental analysis, for $C_{13}H_{10}NO_4Cl$

|  | C | H | N |
|---|---|---|---|
| Calcd. | 55.83 | 3.60 | 5.01 |
| Found | 55.93 | 3.49 | 5.03 |

REFERENCE EXAMPLE 13

In the method of the Reference Example 1, 5-methylanthranilic acid was reacted in the place of anthranilic acid to obtain α-[(2-carboxy-4-methylphenyl-)amino]-γ-butyrolactone, melting point: 199°–200° C.

Elemental analysis, for $C_{12}H_{13}NO_4$

|  | C | H | N |
|---|---|---|---|
| Calcd. | 61.27 | 5.57 | 5.96 |
| Found | 61.13 | 5.61 | 5.99 |

REFERENCE EXAMPLE 14

In the method of the Reference Example 6, α-[(2-carboxy-4-methylphenyl)amino]-γ-butyrolactone was reacted in the place of α-[(2-carboxyphenyl)amino]-γ-butyrolactone to obtain 1'-acetyl-4,5-dihydro-5'-methyl-1'H-spiro[furan-3(3H),2'-indoline]-2,3'-dione, melting point: 176°–177° C.

Elemental analysis, for $C_{14}H_{13}NO_4$

|  | C | H | N |
|---|---|---|---|
| Calcd. | 64.86 | 5.05 | 5.40 |
| Found | 64.66 | 4.95 | 5.43 |

REFERENCE EXAMPLE 15

Under argon sparging, a mixture of 6.64 g of α-[(2-carboxyphenyl)amino]-γ-butyrolactone, 25 g of propionic anhydride and 10 ml of triethylamine was stirred at 140° C for 1 hour. Ice-water was added to the reaction mixture, which was then extracted with chloroform. The extract was washed with water and dried over magnesium sulfate. The chloroform was distilled off and the residue was purified by column chromatography on silica gel. By the above procedure was obtained 6.34 g of 4,5-dihydro-1'-propionyl-1'H-spiro[furan-3(3H),2'-indoline]-2,3'-dione. Recrystallized from ethanol. Melting point: 140°–141° C.

Elemental analysis, for $C_{14}H_{13}NO_4$

|  | C | H | N |
|---|---|---|---|
| Calcd. | 64.86 | 5.05 | 5.40 |
| Found | 65.01 | 4.96 | 5.28 |

What is claimed is:

1. A spiro[cyclopropane-1,2'-indolin]-3'-one compound represented by the formula:

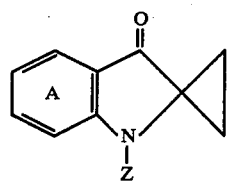

wherein the ring A is unsubstituted or substituted with an alkyl of 1 to 4 carbon atoms, an alkoxy having 1 to 4 carbon atoms, an alkylenedioxy having 1 to 4 carbon atoms, hydroxyl, nitro, amino, formylamino, an alkylcarbonyl amino having 2 to 5 carbon atoms, an arylcarbonyl amino having 7 to 11 carbon atoms or halogen; and Z is selected from the group consisting of (A) hydrogen;

(B) a substituted or unsubstituted alkyl of 1 to 4 carbon atoms, wherein the substituent is selected from the group consisting of an aryl group of 6 to 10 carbon atoms, which aryl group may be further substituted with halogen, an alkyl group of 1 to 4 carbon atoms or an alkoxy group of 1 to 4 carbon atoms; an alkylcarbonyl group having 2 to 5 carbon atoms; formyl; a halogen-substituted or unsubstituted arylcarbonyl group having 7 to 11 carbon atoms; an alkoxy group having 1 to 4 carbon atoms; hydroxyl; an alkoxycarbonyl group having 2 to 5 carbon atoms; carboxyl; an N-substituted or unsubstituted carbamoyl group of the formula -CONPQ wherein each of P and Q is hydrogen or an alkyl group having 1 to 4 carbon atoms; or an amino or a mono- or di-alkylamino group, wherein each alkyl has 1 to 4 carbon atoms; and (C) an unsubstituted acyl group of the formula: $R^1CO-$, $R^2SO_2-$ or $R^3R^4NCO$ in which $R^1$ is hydrogen, an alkyl group having 1 to 4 carbon atoms, an alkoxy group having 1 to 4 carbon atoms or an aryl group having 6 to 10 carbon atoms and $R^2$ is an alkyl group having 1 to 4 carbon atoms or an aryl group having 6 to 10 carbon atoms, and each of $R^3$ and $R^4$ is hydrogen, an alkyl group having 1 to 4 carbon atoms or an aryl group having 6 to 10 carbon atoms, or a substituted acyl group thereof wherein the substituent of the acyl group is amino; a mono- or di-alkylamino wherein the alkyl has 1 to 4 carbon atoms; halogen; an alkyl group having 1 to 4 carbon atoms or an alkoxy group having 1 to 4 carbon atoms, or pharmaceutically acceptable salts of said compound.

2. A spiro [cyclopropane-1,2'-indolin]-3'-one as claimed in claim 1, wherein the ring A is substituted with alkyl having 1 to 4 carbon atoms, an alkoxy having 1 to 4 carbon atoms, an alkylenedioxy having 1 to 4 carbon atoms, hydroxyl, nitro, amino, formylamino, an alkylcaronyl amino having 2 to 5 carbon atoms, an arylcarbonyl amino having 7 to 11 carbon atoms or halogen; and Z is hydrogen or a substituted or unsubstituted alkyl of 1 to 4 carbon atoms, said alkyl being substituted with one of the following groups: an aryl group of 6 to 10 carbon atoms, which aryl group may be further substituted with a halogen, an alkyl of 1 to 4 carbon atoms, or an alkoxy of 1 to 4 carbon atoms, an alkyl carbonyl group of 2 to 5 carbon atoms, an unsubstituted or halogen-substituted arylcarbonyl group having 7 to 11 carbon atoms, alkoxy of 1 to 4 carbon atoms, hydroxyl, an alkoxycarbonyl having 2 to 5 carbon atoms, carboxyl, amino or a mono- or di-alkylamino wherein the alkyl has 1 to 4 carbon atoms.

3. A spiro [cyclopropane-1,2'-indolin]-3'-one as claimed in claim 1, wherein the ring A is substituted with alkyl having 1 to 4 carbon atoms, an alkoxy having 1 to 4 carbon atoms, an alkylenedioxy having 1 to 4 carbon atoms, hydroxyl, nitro, amino, formylamino, an alkylcarbonyl amino having 2 to 5 carbon atoms, an arylcarbonyl amino having 7 11 carbon atoms or halogen; and Z is a substituted or unsubstituted acyl group of the formula: $R^1CO-$ or $R^2SO_2-$ in which $R^1$ is hydrogen, an alkyl group having 1 to 4 carbon atoms, an alkoxy group having 1 to 4 carbon atoms or an aryl group having 6 to 10 carbon atoms and $R^2$ is an alkyl group having 1 to 4 carbon atoms or an aryl group having 6 to 10 carbon atoms, the substituent of the acyl group being halogen, an alkyl group having 1 to 4 carbon atoms, or an alkoxy group having 1 to 4 carbon atoms.

4. A spiro[cyclopropane-1,2'-indolin]-3'-one compound represented by the formula:

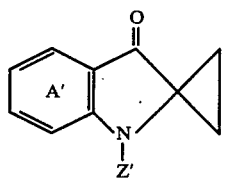

in which the ring A' is a substituted or unsubstituted phenyl ring, wherein the substituent is an alkyl group having 1 to 4 carbon atoms, an alkoxyl group having 1 to 4 carbon atoms or halogen, the number of substituents being one or two; and wherein Z' is selected from the group consisting of
(A) hydrogen;
(B) a substituted or unsubstituted alkyl group having 1 to 4 carbon atoms wherein the substituent is a di-alkylamino group, each alkyl of the di-alkylamino group having 1 to 4 carbon atoms; an alkoxy-carbonyl group having 2 to 5 carbon atoms; benzoyl; a benzoyl group substituted by halogen; phenyl; a phenyl group substituted by an alkoxy group having 1 to 4 carbon atoms; hydroxyl or carboxyl; and
(C) an acyl group selected from
(1) an acyl group of the formula: $R^1CO-$ in which $R^1$ is hydrogen; an alkoxy group having 1 to 4 carbon atoms; phenyl; a phenyl group substituted by halogen; or a substituted or unsubstituted alkyl group having 1 to 4 carbon atoms in which the substituent of the alkyl is a di-alkylamino group and wherein each alkyl of the di-alkylamino group has 1 to 4 carbon atoms;
(2) an acyl group of the formula: $R^2SO_2-$ in which $R^2$ is an alkyl group having 1 to 4 carbon atoms, phenyl or a phenyl group substituted by an alkyl group having 1 to 4 carbon atoms; and
(3) an acyl group of the formula: $R^3R^4NCO-$ in which each of $R^3$ and $R^4$ is hydrogen or an alkyl group having 1 to 4 carbon atoms, or pharmaceutically acceptable salts of said compound.

5. A spiro [cyclopropane-1,2'-indolin]-3'-one of the formula:

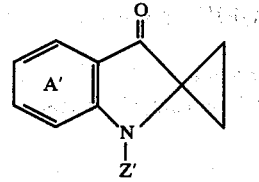

in which the ring A' is substituted or unsubstituted, the substituent being an alkyl having 1 to 4 carbon atoms, an alkoxy of 1 to 4 carbon atoms or halogen, wherein the number of the substituents is one or two; and Z' is hydrogen; a substituted or unsubstituted alkyl having 1 to 4 carbon atoms, said substituent of the alkyl being one of the following groups: a di-alkylamino, each alkyl of the dialkylamino having 1 to 4 carbon atoms, an alkoxy-carbonyl having 2 to 5 carbon atoms, benzoyl, a benzoyl group substituted by halogen, phenyl, a phenyl group substituted by an alkoxy group having 1 to 4 carbon atoms, hydroxyl or carboxyl, an acyl group of the formula: $R^1CO-$ in which $R^1$ is hydrogen, an alkoxy of 1 to 4 carbon atoms, phenyl, a phenyl substituted by halogen, or an unsubstituted alkyl group having 1 to 4 carbon atoms, or Z' is an acyl group of the formula: $R^2SO_2-$ in which $R^2$ is an alkyl of 1 to 4 carbon atoms, phenyl or phenyl substituted by alkyl of 1 to 4 carbon atoms or its pharmaceutically acceptable salt.

6. A compound as claimed in claim 1, namely 1'H-spiro[cyclopropane-1,2'-indolin]-3'-one.

7. A compound as claimed in claim 1, namely 1'-acetyl-1'H-spiro[cyclopropane-1,2'-indolin]-3'-one.

8. A compound as claimed in claim 1, namely 1'-formyl-1'H-spiro[cyclopropane-1,2'-indolin]-3'-one.

9. A compound as claimed in claim 1, namely 1'-(4-chlorobenzoyl)-1'H-spiro[cyclopropane-1,2'-indolin]-3'-one.

10. A compound as claimed in claim 1, namely 1'-methyl-1'H-spiro[cyclopropane-1,2'-indolin]-3'-one.

11. A compound as claimed in claim 1, namely 1'-acetyl-5'-methoxy-1'H-spiro[cyclopropane-1,2'-indolin]-3'-one.

12. A compound as claimed in claim 1, namely 1'-acetyl-5', 6'-dimethoxy-1'H-spiro[cyclopropane-1,2'-indolin]-3'-one.

13. A compound as claimed in claim 1, namely 1'-acetyl-5'-chloro-1'H-spiro[cyclopropane-1,2'-indolin]-3'-one.

14. A compound as claimed in claim 1, namely 1'-(4-methoxybenzyl)-1'H-spiro[cyclopropane-1,2'-indolin]-3'-one.

15. A compound as claimed in claim 1, namely 1'-(3-diemthylaminopropyl)-1'H-spiro[cyclopropane-1,2'-indolin]-3'-one.

16. A compound as claimed in claim 1, namely 1'-[3-(4-fluorobenzoyl)-propyl]-1'H-spiro[cyclopropane-1,2'-indolin]-3'-one.

17. A compound as claimed in claim 1, namely 1'-(3-hydroxypropyl)-1'H-spiro[cyclopropane-1,2'-indolin]-3'-one.

18. A compound as claimed in claim 1, namely 1'-carboxymethyl-1'H-spiro[cyclopropane-1,2'-indolin]-3'-one.

19. A compound as claimed in claim 1, namely 1'-carbamoyl-1'H-spiro[cyclopropane-1,2'-indolin]-3'-one.

20. A compound as claimed in claim 1, namely 1'-(N-methylcarbamoyl)-1'H-spiro[cyclopropane-1,2'-indolin]-3'-one.

21. A compound as claimed in claim 1, namely 1'-acetyl-5'-methyl-1'H-spiro[cyclopropane-1,2'-indolin]-3'-one.

22. A compound as claimed in claimed 1, namely 1'-propionyl-1'H-spiro[cyclopropane-1,2'-indolin]-3'-one.

23. A compound as claimed in claim 1, namely 1'-isobutyryl-1'H-spiro[cyclopropane-1,2'-indolin]-3'-one.

24. A compound as claimed in claim 1, namely 1'-dimethylaminoacetyl-1'H-spiro[cyclopropane-1,2'-indolin]-3'-one.

25. A compound as claimed in claim 1, namely 1'-(2-dimethylaminopropionyl)-1'H-spiro[cyclopropane-1,2'-indolin]-3'-one.

26. A compound as claimed in claim 1, namely 1'-ethoxycarbonyl-1'H-spiro[cyclopropane-1,2'-indolin]-3'-one.

27. A compound as claimed in claim 1, namely 1'-mesyl-1'H-spiro[cyclopropane-1,2'-indolin]-3'-one.

28. A compound as claimed in claim 1, namely 1'-tosyl-1'H-spiro[cyclopropane-1,2'-indolin]-3'-one.

29. A compound as claimed in claim 1, namely 1'-(2-dimethylaminoethyl)-1'H-spiro[cyclopropane-1,2'-indolin]-3'-one.

30. A compound as claimed in claim 1, namely 1'-(2-diethylaminoethyl)-1'H-spiro[cyclopropane-1,2'-indolin]-3'-one.

31. A compound as claimed in claim 1, namely 1'-isobutyl-1'H-spiro[cyclopropane-1,2'-indolin]-3'-one.

32. A method for the production of a spiro[cyclopropane-1,2'-indolin]-3'-one of the formula:

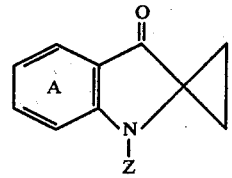

wherein the ring A is a substituted or unsubstituted phenyl ring and Z is hydrogen, a substituted or unsubstituted alkyl group as defined in claim 1 or a substituted or unsubstituted acyl group or pharmaceutically acceptable salt thereof, which comprises subjecting a 4,5-dihydrospiro[furan-3(3H), 2'-indoline]-2,3'-dione represented by the general formula:

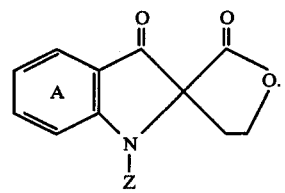

* * * * *